United States Patent [19]

Koob et al.

[11] Patent Number: 4,972,852
[45] Date of Patent: Nov. 27, 1990

[54] PATIENT POSITIONING DEVICE

[75] Inventors: Lothar Koob, Roettenbach; Hermann Riedl; Guenter Theil, both of Erlangen; Edgar Tschunt, Rathsberg, all of Fed. Rep. of Germany

[73] Assignee: Siemens Aktiengesellschaft, Berlin and Munich, Fed. Rep. of Germany

[21] Appl. No.: 449,520

[22] Filed: Dec. 5, 1989

Related U.S. Application Data

[63] Continuation of Ser. No. 694,577, Jan. 24, 1985, abandoned.

[30] Foreign Application Priority Data

May 4, 1984 [DE] Fed. Rep. of Germany ....... 3416556

[51] Int. Cl.$^5$ ............................................. A61B 5/00
[52] U.S. Cl. ................................ 128/653 R; 269/322; 128/653 A
[58] Field of Search ............... 128/653, 731, 696, 639, 128/644; 269/322; 378/209

[56] References Cited

U.S. PATENT DOCUMENTS

| | | | |
|---|---|---|---|
| 2,860,627 | 11/1958 | Harden et al. | 128/731 |
| 3,541,334 | 11/1970 | Sobolewski et al. | 250/91 |
| 4,323,076 | 4/1982 | Sams | 128/644 |
| 4,404,974 | 9/1983 | Titus | 128/696 |
| 4,411,270 | 10/1983 | Damadian | 128/653 |
| 4,425,922 | 1/1984 | Conti et al. | 128/696 |
| 4,498,480 | 2/1985 | Mortensen | 128/644 |

Primary Examiner—Ruth S. Smith
Attorney, Agent, or Firm—Mark. H. Jay

[57] ABSTRACT

The invention relates to a patient positioning device with a pedestal on which a patient positioning plate is mounted for longitudinal displacement. At least one signal transmission device is to be applied to or used by the patient. On the patient positioning plate is provided at least one plug device for connection of the cable of the signal transmission device. A cable securely installed on the patient positioning plate leads from the plug device to the fixed apparatus part, the cable forming a loop to permit longitudinal displacement of the patient positioning plate.

2 Claims, 3 Drawing Sheets

PATIENT POSITIONING DEVICE

CROSS-REFERENCE TO RELATED APPLICATION

This is a contiuation of application Ser. No. 06/649,577 filed Jan. 24, 1985 now abandoned.

BACKGROUND OF THE INVENTION

The invention relates to a patient positioning device with a pedestal on which a patient positioning plate is mounted for longitudinal displacement, and with at least one signal transmission device which is connected via a cable to a fixed point elsewhere on the apparatus.

A patient positioning device of this kind is used for example to introduce a patient into a magnet for making magnetic resonance images. For the deflection of certain particles, e.g. protons, a radio-frequency transmitting and receiving coil is used which, after cutoff of the excitation pulse, forms a signal caused by the return of the excited particles to their initial (unexcited) positions. For measurement in the pateient's head region, for example, this coil is placed over the head and is then connected to a fixed point on the apparatus by a flexible cable. If this flexible cable leads directly to the fixed point, the cable may hit the edge of the magnet and be damaged as the patient positioning plate is moved into the magnet. Also, the attending personnel are hindered by the cable.

One object of the invention is to design a patient positioning device in such a way that the cable between the signal transmission device and the fixed apparatus part is short and does not interfere with the examination procedure.

Another object is to generally improve on the prior art.

According to the invention, there is mounted on at the patient positioning plate at least one plug device to which one end of the cable may be connected. From the plug device, a cable securely installed on the patient positioning plate leads to the fixed point, the cable forming a loop to permit longitudinal displacement of the patient positioning plate. The fixed point is located in the region of the pedestal, so that the cable which is installed between it and the plug device and which moves along with the longitudinal displacement of the patient positioning plate is not in the way. The cable between the signal transmission device and the plug device is kept short and does not lead away from the patient positioning device, thus avoiding hinderence to attending personnel before and during the examination.

The invention will be better understood with reference to the following drawings and the detailed description of preferred embodiments.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
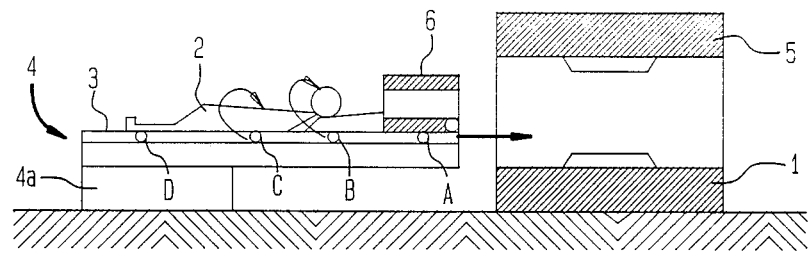
FIGS. 1 and 2 are schematic representations of magnetic resonance apparatus in which a preferred embodiment of the invention is illustrated as connected to two different sets of electrical equipment.
Figure 2:
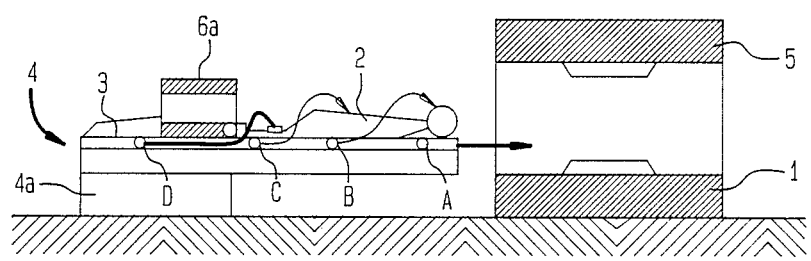

In FIGS. 1 and 2, the magnet 1 of a magnetic resonance machine is shown; the machine is secured on the floor of a treatment room. For examination, a patient 2 is pushed by means of the patient positioning plate 3 of a patient positioning device 4 into the cylindrical interior 5 of magnet 1. In FIG. 1 a coil 6 is shown which serves to excite the hydrogen nuclei in a predetermined region of the patient 2, namely in the region of the head. To this end, coil 6 is placed around the patient's head, and the patient 2 is then inserted on plate 3 into the interior 5. The magnet 1 orients the hydrogen nuclei in the patient; these nuclei are then deflected by a high-frequency pulse in coil 6. Coil 6 serves also to detect the swinging back of the hydrogen nuclei, so that from the measured signals an image of the examined layer of patient 2 can be derived.

As shown in FIG. 2, a coil 6a is provided which can be placed around the body of patient 2, i.e. which serves for, e.g., examination in the region of the thorax. There is also a separate coil 7 which serves for exciting and examining certain body parts, e.g. the knee.

FIGS. 1 and 2 show that the patient positioning plates 3 has plug devices or plus-type connectors A, B, C and D, to which the coils 6, 6a, 7 as well as other signal transmission devices can be connected by cables. Plug device A serves to connect coils 6, 6a; plug device B serves to connect an earphone or headphone; plug connection C serves to connect EKG electrodes, respiration measuring devices, pulse measuring devices and the like; and plug device D serves to connect the separate coil 7.

Figure 3:
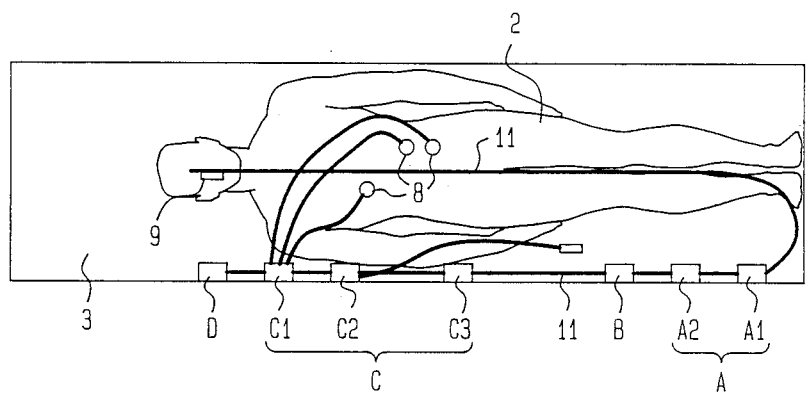
FIG. 3 is a top view of the preferred embodiment.

FIG. 3 shows the top of the patient positioning plate 3. On the patient 2 three electrodes 8 for EKG pickup are applied, which go to the plug device C1. Also leading to the plug connected C1 is a line for a respiration probe 9. The plug device A is also divided, namely into two plug devices A1 and A2. All plug devices A to D are interconnected by a cable 11, which is securely installed under the patient positioning plate 3.

Figure 4:
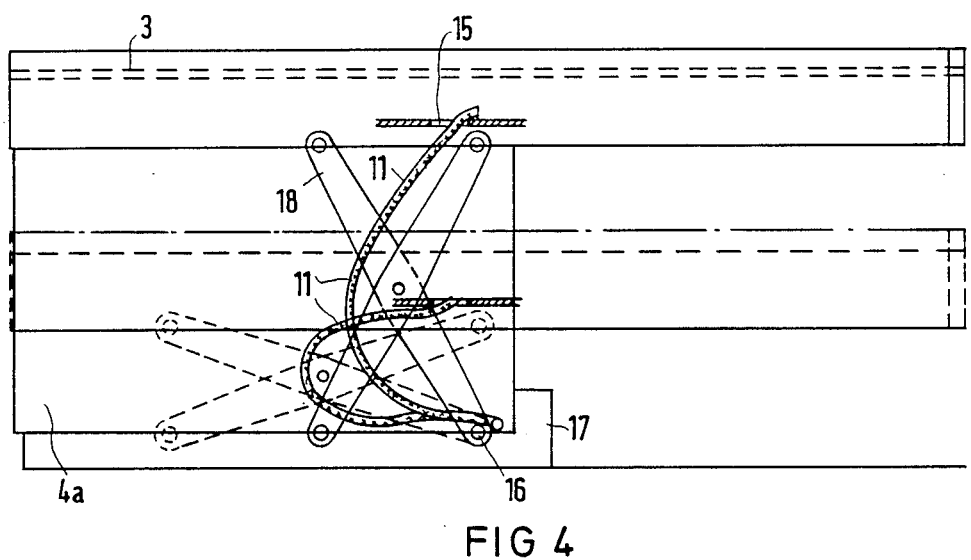
FIG. 4 is a side view of the preferred embodiment.
Figure 5:
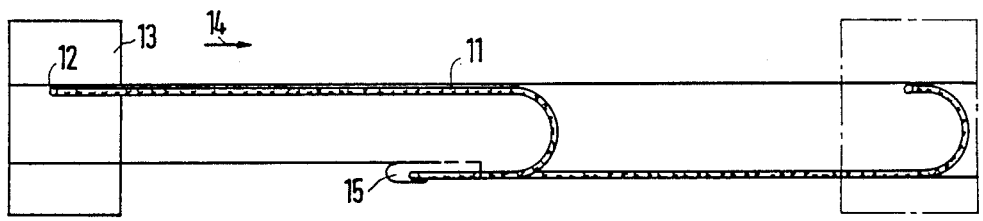
FIG. 5 is a detail view of a portion of the preferred embodiments.
Figure 6A:
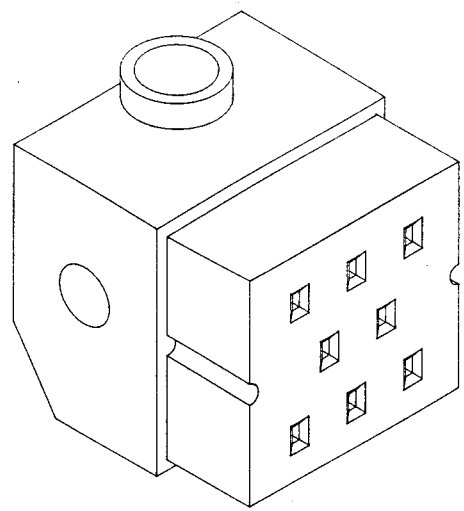
FIGS. 6a–6b show the plug-type connector which is used in accordance with the invention
Figure 6B:
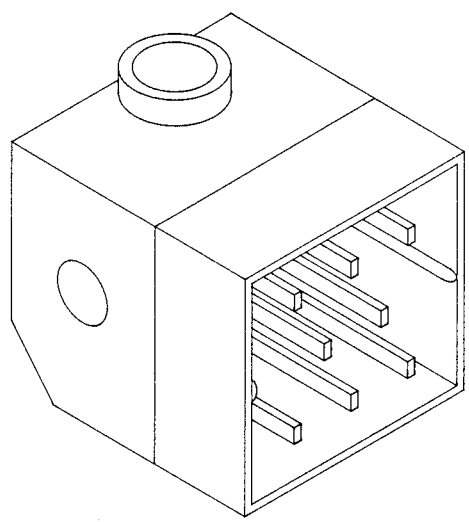

FIG. 5 shows that the cable 11 is attached at a point 12 to a carriage 13 which carries the patient positioning plate 3. In FIG. 5, the patient positioning plate 3 is omitted for greater clarity. Carriage 13 can be moved from the position shown in solid lines into the position shown in dash-dot lines. Cable 11 forms a loop which, as carriage 13 moves in the direction of arrow 14, also moves under the patient positioning plate 3. FIG. 5 is taken from the above patient positioning device 4. The cable 11 is passed through an opening 15 (which can be seen also in FIG. 4) and leads via a point 16 to a fixed apparatus part 17. Between points 15 and 16 the cable 11 forms a loop, so that the patient positioning plate 3 can be raised and lowered by means of a hoisting device 18.

FIG. 4, the parts 11 and 18 are shown, for greater clarity, in solid lines, although they are concealed by the paneling of the pedestal 4a.

Those skilled in the art will understand that changes can be made in the preferred embodiments here described, and that these embodiments can be used for other purposes. Such changes and uses are within the scope of the invention, which is limited only by the claims which follow.

What is claimed is:

1. An improvement to a patient positioning apparatus of a type in which a patient postioning plate is mounted on a pedestal for longitudinal displacement and in which at least one electrical connection is to be made between (a) an electrical device which is moved together with the plate and (b) a fixed point, the improvement comprising:

a plug-type connector having first and second mating parts, the first part being mounted to the patient positioning plate and the second part being connected to an electrical cable leading to said device; and a flexible electrical cable connecting said first part of said connector and said fixed point, said flexible electrical cable forming a loop which is repositioned as the positioning plate is moved.

2. The improvement of claim 1, wherein the flexible electrical cable is located beneath the patient positioning plate and is generally maintained in a plane during movement of said plate.

* * * * *